United States Patent [19]

Mikos et al.

[11] Patent Number: 5,514,378
[45] Date of Patent: May 7, 1996

[54] BIOCOMPATIBLE POLYMER MEMBRANES AND METHODS OF PREPARATION OF THREE DIMENSIONAL MEMBRANE STRUCTURES

[75] Inventors: Antonios G. Mikos, Houston, Tex.; Georgios Sarakinos, Boston, Mass.; Joseph P. Vacanti, Winchester, Mass.; Robert S. Langer, Newton, Mass.; Linda G. Cima, Lexington, Mass.

[73] Assignees: Massachusetts Institute of Technology, Cambridge; Children's Medical Center Corporation, Boston, both of Mass.

[21] Appl. No.: 12,270

[22] Filed: Feb. 1, 1993

[51] Int. Cl.$^6$ .................................. C08J 5/20; A61F 2/00
[52] U.S. Cl. ............................ 424/425; 424/426; 521/27
[58] Field of Search ............................... 521/27; 424/426, 424/425

[56] References Cited

U.S. PATENT DOCUMENTS

| | | |
|---|---|---|
| 4,060,081 | 11/1977 | Yannas et al. . |
| 4,391,909 | 7/1983 | Lim .......................................... 435/178 |
| 4,458,678 | 7/1984 | Yannas et al. . |
| 4,520,821 | 6/1985 | Schmidt et al. . |
| 4,897,267 | 1/1990 | Bontemps et al. ....................... 424/426 |
| 5,041,138 | 8/1991 | Vacanti et al. ........................... 424/458 |
| 5,064,866 | 11/1991 | Toyomoto et al. ........................ 521/27 |

FOREIGN PATENT DOCUMENTS

| | | | |
|---|---|---|---|
| 1268733 | 1/1989 | Japan .................................... | 521/27 |
| 678407 | 9/1991 | Switzerland ............................. | 521/27 |
| 9072604 | 11/1990 | WIPO .................................... | 424/426 |

OTHER PUBLICATIONS

Vacanti, J. P. "Beyond Transplantation", *Arch. Surg.*, 123:545–549 (1988).
Vacanti, J. P. "Selective Cell Transplantation Using Bioabsorbable Artificial Polymers as Matrices", *Journal of Pediatric Surgery*, 23(1):3–9 (1988).

*Primary Examiner*—Peter F. Kulkosky
*Attorney, Agent, or Firm*—Arnall Golden & Gregory

[57] ABSTRACT

Biocompatible porous polymer membranes are prepared by dispersing salt particles in a biocompatible polymer solution. The solvent in which the polymer is dissolved is evaporated to produce a polymer/salt composite membrane. The polymer can then be heated and cooled at a predetermined constant rate to provide the desired amount of crystallinity. Salt particles are leached out of the membrane by immersing the membrane in water or another solvent for the salt but not the polymer. The membrane is dried, resulting in a porous, biocompatible membrane to which dissociated cells can attach and proliferate. A three-dimensional structure can be manufactured using the polymer membranes by preparing a contour drawing of the shape of the structure, determining the dimensions of thin cross-sectional layers of the shape, forming porous polymer membranes corresponding to the dimensions of the layers, and laminating the membranes together to form a three-dimensional matrix having the desired shape.

9 Claims, 7 Drawing Sheets

BIOCOMPATIBLE POLYMER MEMBRANES AND METHODS OF PREPARATION OF THREE DIMENSIONAL MEMBRANE STRUCTURES

The present invention relates to the field of polymer science and more particularly to biodegradable polymer membranes, methods of preparation thereof, and use in preparation of devices for transplantation and implantation of cells and tissues.

BACKGROUND OF THE INVENTION

Loss of organs or appendages can result from congenital defects, injury or disease. Many times treatment with drugs or surgery is not in itself sufficient and the patient is severely disabled. For example, burn victim are often disfigured by the loss of cartilage in appendages such as the nose, ears, fingers or toes. One approach for treatment has been to transplant donor organs or tissue into the patient, or graft tissues from one area of the patient to another. However, there is a tremendous shortage of donor organs, most of which must come from a recently deceased individual. Moreover, these tissues have generally not been useful for correction of defects such as worn or torn cartilage.

Cell transplantation has been explored as an alternative to various means of replacing tissue function. Using this approach, individual cells are harvested from a healthy section of donor tissue, isolated and implanted in the patient at a desired site. Cell transplantation has several advantages over whole organ transplantation. Because the isolated cell population can be expanded in vitro using cell culture techniques, only a very small number of donor cells are needed to prepare an implant. Consequently, the living donor need not sacrifice an entire organ. The use of isolated cells also allows removal of other cell types which may be the target of immune responses, thus diminishing the rejection process. In addition, major surgery on the recipient and donor and its inherent risks are avoided. Finally, the cost of the procedure may be significantly reduced.

There have been a number of attempts to culture dissociated tissue and implant the cultured cells directly into the body. For example, transplantation of pancreatic tissue, either as a whole organ or as a segment of an organ, into the diabetic patient has been attempted. However, such implants do not form three dimensional structures, and the cells are lost by phagocytosis and attrition.

Isolated cells cannot form new tissues on their own. Most cells have a requirement for attachment to a surface in order to replicate and function. They require specific environments which very often include the presence of supporting material to act as a template for growth. Three dimensional scaffolds are used to mimic their natural counterparts, the extracellular matrices of the body. They serve as both a physical support and an adhesive substrate for isolated parenchymal cells during ↑in vitro↑ culture and subsequent implantation.

A method for forming artificial skin by seeding a fibrous lattice with epidermal cells is described in U.S. Pat. No. 4,485,097 to Bell, which discloses a hydrated collagen lattice that, in combination with contractile agents such as platelets and fibroblasts and cells such as keratinocytes, is used to produce a skin-like substance. U.S. Pat. No. 4,060,081 to Yannas et al. discloses a multilayer membrane for use as a synthetic skin that is formed from an insoluble modified collagen material that is very slowly degradable in the presence of body fluids and enzymes. U.S. Pat. No. 4,458,678 to Yannas et al. discloses a process for making a skin-like material wherein a biodegradable fibrous lattice formed from collagen cross-linked with glycosaminoglycan is seeded with epidermal cells. Unfortunately, there is a lack of control over the composition and configuration of the latter matrix because it is primarily based on collagen. In addition, the degradation is quite variable because the collagen is degraded by enzymatic action and hydrolysis.

U.S. Pat. No. 4,520,821 to Schmidt describes a similar approach to make linings to repair defects in the urinary tract. Epithelial cells are implanted onto the surface a liquid impermeable synthetic polymeric matrix where they form a monolayer lining on the matrix. This approach is limited to the production of relatively thin structures.

Vacanti, et al., "Selective cell transplantation using bioabsorbable artificial polymers as matrices" *J. Pediat. Surg.* 23, 3–9 (1988) and Vacanti, "Beyond Transplantation" *Arch. Surg.* 123, 545–549 (1988), describe an approach for making new organs for transplantation which was not subject to the same limitations as the work of Yannas and Burke, i.e., it was not limited to the construction of very thin organs such as skin. Vacanti, et al., recognized that cells require a matrix for attachment and support if they are to survive following implantation, that a minimum number of cells was essential for function in vivo, and that the matrix must be porous enough to allow nutrients and gases to reach all of the cells on and within the matrix by diffusion, until the matrix-cell structure was vascularized. Moreover, they recognized the advantage of using synthetic biodegradable polymer substrates to form a scaffold that mimics its natural counterparts, the extracellular matrices (ECM) of the body, serving as both a physical support and an adhesive substrate for isolated parenchymal cells during in vitro culture, and subsequent implantation, degrading as the cells begin to secrete they own ECM support. Subsequent studies have demonstrated that even better results are obtained when the matrix is first implanted, prevascularized, and then seeded with cells. Most matrices used in the earlier work are modifications of materials already available, such as surgical sutures and meshes. This latter approach, however, requires new matrix configurations which are optimal for vascularization, yet resistant to compression, with sufficient porosity and interconnected interstitial spacings to allow injected cells to become dispersed throughout the matrix.

As a result, there remains a need for improved polymeric matrices that provide guided support for the cells to be implanted, especially in the reconstruction of structural tissues like cartilage and bone, where tissue shape is integral to function. In particular, there is a need for a matrix that is relatively easy to manufacture in a shape appropriate for a particular patient, which can be constructed to degrade in synchrony with the growth of the cells seeded thereon. A uniformly distributed and interconnected pore structure is important so that an organized network of tissue constituents can be formed. Therefore, these scaffolds must be processable into devices of varying thickness and shape.

To date, no processing techniques exist to prepare three-dimensional biocompatible foams with complex and delicate shapes, thereby limiting the potential of organ regeneration by cell transplantation.

It is therefore an object of the present invention to provide a method of preparing highly porous, biocompatible polymer membranes, and the resulting membranes.

It is a further object of the present invention to provide a highly porous, biocompatible three-dimensional matrix having a desired anatomical shape.

It is another object of the present invention to provide a three-dimensional biocompatible matrix for reconstruction of anatomically-shaped tissues, especially cartilage and bone.

SUMMARY OF THE INVENTION

Biocompatible porous polymer membranes are prepared by dispersing particles in a biocompatible polymer solution. Examples of preferred biodegradable polymers include polyorthoesters, poly(lactic acid), poly(DL-lactic-co-glycolic acid) (PLGA), and blends thereof. Particles can be formed of salts, polysaccharides, proteins, polymers other than the matrix polymers or other-non toxic materials which are soluble in a solvent which does not dissolve the polymers used to form the matrix. The solvent in which the polymer is dissolved is evaporated to produce a polymer/particle composite membrane. The polymer can then be heated and cooled at a predetermined constant rate to provide the desired amount of crystallinity. Salt particles are dissolved out of the membrane by immersing the membrane in water or another solvent for the particles but not the polymer. The membrane is dried, resulting in a porous, biocompatible membrane to which dissociated cells can attach and proliferate.

A three-dimensional structure can be manufactured using the polymer membranes by preparing a contour drawing of the shape of the structure, determining the dimensions of thin cross-sectional layers of the shape, forming porous polymer membranes corresponding to the dimensions of the layers, and laminating the membranes together to form a three-dimensional matrix having the desired shape. The membranes are laminated by wetting one side of each of two membranes, placing one membrane on top of the other with the wetted surfaces touching, and applying sufficient force to affix the membranes. The laminating procedure is repeated until all of the membranes are laminated together to produce the desired three-dimensional shape. Excess portions of the matrix can be excised with a scalpel or other instrument to create crevices or openings as desired.

The resulting three-dimensional foam or shape is a porous, biocompatible matrix to which cultured cells can attach and proliferate, and can be used for organ transplantation or reconstructive surgery. Methods for optimal introduction of dissociated cells into these structures are exemplified.

BRIEF DESCRIPTION OF THE DRAWINGS

FIG. 2A is a graph showing the relationship between the porosity of the membranes as a function of the initial sodium chloride weight fraction. The open square symbol represents salt having a diameter between 0 and 53 microns. The open circle represents salt having a diameter between 53 and 106 microns. The open triangle represents salt having a diameter between 106 and 150 microns. The black square represents salt having a diameter between 150 and 250 microns. The black circle represents salt having a diameter between 250 and 500 microns. FIG. 2B is a graph showing the relationship between the surface to volume ratio of the membranes and the initial sodium chloride weight fraction. The symbols are the same as in FIG. 2B.

FIG. 6A is a side view. FIG. 6B is a top view.

DETAILED DESCRIPTION OF THE INVENTION

Methods described herein relate to the manufacture of polymeric membranes having a thickness that is preferably between 500 and 2000 microns, formed of biocompatible, preferably biodegradable, synthetic polymers, which have interconnected interstices with a pore size range between greater than 0 and 500 microns, most preferably for seeding of cells, in excess of 100 to 150 microns; and the manufacture of three dimensional structures from these materials. The three dimensional structures are formed by layering the membranes until a laminated structure is assembled in a desired shape. A particular advantage of the use of the membranes is that polymers with different properties, and membranes with different porosities, can be used to assemble the structure, much as occurs in nature.

Method of Manufacture of Polymeric Membranes

Figure 1:
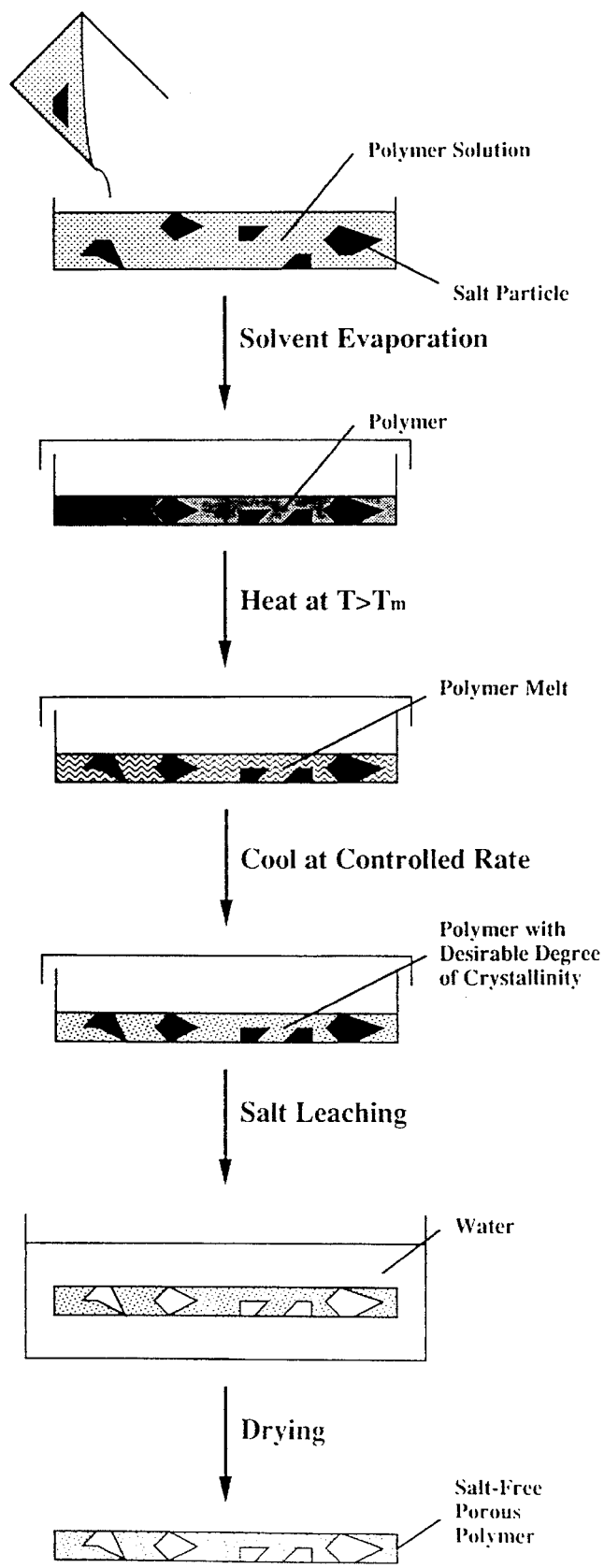
FIG. 1 is a schematic representation of the method of preparation of the highly porous, biocompatible polymer membranes.

A particulate-leaching technique for preparation of the highly porous, biodegradable polymer membranes is provided. The technique is shown schematically in FIG. 1. The resulting membranes are highly porous, greater than 90% porous, biocompatible, and biodegradable, suitable for attachment and proliferation of dissociated cells.

Particle dispersion in polymer Polymers.

Particles are dispersed in a solution of biocompatible polymer. Either biodegradable polymers, which are preferred for most applications, or non-biodegradable polymers, can be used.

Poly(alpha esters) such as poly(lactic acid), poly(glycolic acid), and their copolymers are an important class of biodegradable polymers. These are among the synthetic polymers approved for human clinical use. They are presently utilized as surgical suture materials and in controlled release devices, as well as in other medical and pharmaceutical applications. They are biocompatible and their degradation products are low molecular weight compounds, such as lactic acid and glycolic acid, which enter into normal metabolic pathways. Furthermore, copolymers of poly(lactic-co-glycolic acid) offer the advantage of a large spectrum of degradation rates from a few days to years by simply varying the copolymer ratio of lactic acid to glycolic acid.

The preferred biodegradable polymers are lactic acid polymers such as poly(L-lactic acid) (PLLA), poly(DL-lactic acid) (PLA), and poly(DL-lactic-co-glycolic acid) (PLGA). The co-monomer (lactide:glycolide) ratios of the poly(DL-lactic-co-glycolic acid) are preferably between 100:0 and 50:50. Most preferably, the co-monomer ratios are between 85:15 (PLGA 85:15) and 50:50 (PLGA 50:50). Blends of PLLA with PLGA, preferably PLGA 85:15 and PLGA 50:50, are also used to prepare polymer membranes. Other representative polymers include polyorthoesters, and although not preferred for mechanical characteristics, polyanhydrides. The preferred biodegradable polymers are all degraded by hydrolysis. It is possible, however, to use other materials which degrade enzymatically, although this is not preferred due to the greater difficulty involved in processing and less uniformity in degradation in vivo.

Examples of non-biodegradable materials include ethylene vinyl acetate, poly(vinyl alcohol).

The particles can be any salt that forms crystals or particles having a diameter less than 500 microns, which is easily removed from and does not react with the polymer, and is non-toxic if some residue remains in the polymer after leaching. Examples are proteins such as gelatin and agarose, starches, polysaccharides such as alginate and other polymers. Preferably, the salt is a sodium salt, such as sodium chloride, sodium tartrate and sodium citrate, and other water soluble salts or compounds not soluble in the polymer solvent, for example, chloroform or methylene chloride. The most preferred salt is sodium chloride.

Preferably, the particles are first sieved through a mesh or a series of screens to provide particles of relatively uniform diameter. The diameter of the particles is between 0 and 500 microns. Preferably, the diameter of the salt particles is between 100 and 500 microns. Most preferably, the diameter of the particles is between 250 and 500 microns, particularly for preparing a membrane for hepatocyte or chondrocyte cell transplantation.

The particles are added to a polymer solution in the range from 4.2 to 21.1 weight percent. The initial salt weight fraction is preferably between 0.5 and 0.9 dry weight percent. The corresponding initial polymer dry weight fraction is therefore between 0.1 and 0.5 weight percent. The initial salt weight fraction is instrumental in determining the characteristics of the polymer membrane.

Polymer solvents.

The polymer is dissolved in a solvent that does not adversely affect the polymer or the salt, most preferably a volatile organic solvent. The relative amount of solvent will have a minimal effect on the structure of the produced membranes, but will affect the solvent evaporation time. Preferably, the solvent contains a chlorine molecule, such as the solvents chloroform and methylene chloride. The preferred solvent is chloroform.

Shaping of the Membranes.

The polymer solution can be cast into any appropriate mold, with the dried polymer membrane retaining the shape of the mold. The solvent is evaporated from the salt and polymer mixture over a period of time, preferably forty-eight hours, at room temperature. Any residual solvent is subsequently removed by lyophilization. The resulting mixture will be in the form of a polymer membrane interspersed with particles.

Membrane Crystallinity

The mixture can be heated after removal of the solvent to decrease or increase the crystallinity of the membrane. Alternatively, particles can be directly dissolved out of the membrane in the absence of heat to prepare membranes having a high crystallinity. Membranes having high crystallinity, i.e., greater than 20%, will be stronger and will therefore degrade slower than membranes having reduced crystallinity.

To obtain membranes with a lower crystallinity and a faster rate of degradation after implantation, the salt and polymer mixture is heated at a temperature that will melt the polymer without affecting the particles. Preferably, the mixture is heated at a temperature between 15° and 20° C. higher than the melting temperature ($T_m$) of the polymer. A temperature approximately 15° C. higher than the polymer melting temperature is most preferred. The mixture is heated for a sufficient amount of time to uniformly melt the polymer. One hour is normally sufficient.

The melted polymer is cooled to room temperature at a predetermined constant rate. The rate of cooling will also affect crystallinity and the rate of biodegradation after implantation. A faster cooling rate will produce a membrane having a lower degree of crystallinity. Preferably, the mixture is cooled at a rate between 5° and 20° C. per minute. The preferred cooling rate for the formation of a membrane for use in liver or cartilage cell transplants is large enough to yield amorphous PLLA membranes. The mixture cooled at the predetermined rate will have the desired degree of crystallinity for the intended use.

Particle leaching

The resulting crystallized polymer and particle composite membrane is immersed in a liquid in which the particle is soluble for a sufficient amount of time to allow leaching of substantially all of the particle, but which does not dissolve or detrimentally alter the polymer. The preferred liquid is water, most preferably distilled-deionized water, which does not dissolve the polymer nor cause measurable hydrolysis of the polymer within the time required for processing. Preferably, the particle is leached out of the membrane in a vessel containing distilled-deionized water for a period of forty-eight hours for a polymer such as PLLA or ninety-six hours for PLGA, and the water is changed approximately every twelve hours. The vessel can be placed in a heated waterbath or incubator and shaken to enhance particle leaching. Most preferably, the vessel of water is placed in a waterbath heated to approximately 37° C. and is shaken at approximately 100 rpm to enhance the leaching process.

Removal of the particle will create a polymer membrane having a plurality of relatively evenly spaced interconnected interstitial spaces or pores, formerly occupied by the particle crystals, into which cells can migrate, attach, and proliferate to create an organ or appendage. The porosity of the membrane is very high, greater than 90%.

The polymer membrane is dried for a sufficient amount of time to remove any water that may be occupying the pores. Preferably, the polymer membrane is air-dried for approximately twenty-four hours followed by vacuum-drying with a lyophilizer for approximately forty-eight hours.

Membrane characteristics

The membranes are essentially particle-free. The amount of residual particle depends on the initial particle weight fraction and particle size (i.e., the lower the initial particle weight fraction, the higher the percentage of residual particle). When the particle is a sodium salt, the residual sodium fraction is generally less than 0.001.

The porosity of membranes is dependent on the initial particle weight fraction. As the initial particle weight fraction increases, the porosity of the membranes also increases. The pore size (or interstitial space) of the membranes is directly proportional to particle size.

As described above, the morphology of the membranes depends largely upon the initial particle weight fraction. Above a threshold value of 70 wt %, the membranes are isotropic. Particle weight fractions lower than 70 wt % produce an asymmetric membrane consisting of a dense skin and a porous base.

As described in the examples below, a particulate-leaching method was developed to prepare highly porous biodegradable polymer membranes, which involves the casting of polymer/particle composite membranes followed by the dissolution of the salt. Poly(L-lactic acid) porous membranes of controlled porosity, surface/volume ratio, and crystallinity were prepared with sodium chloride, sodium tartrate, or sodium citrate sieved particles. For salt weight fractions of 50 and 60 wt%, asymmetric membranes were formed independent of salt particle size. When 70–90 wt % salt was used, the membranes were homogeneous with interconnected pores. The membrane properties were independent of the salt type and were only related to the salt weight fraction and particle size. The porosity increased with the salt weight fraction, and the median pore diameter increased as the salt particle size increased. The polymer/salt composite membranes could be quenched or annealed to yield amorphous or semi-crystalline foams with the desired crystallinity. All foams were 99.9 wt % salt-free and had porosities as high as 0.93 and median pore diameters up to 150 µm. These foams offer many advantages for use as substrates for cell transplantation and tissue regeneration.

EXAMPLE 1

Manufacture of Porous Polymeric Membranes. Materials.

Poly(L-lactic acid) (PLLA) was supplied by Polysciences (Warrington, Pa.). Granular sodium chloride, sodium tartrate, and sodium citrate (Mallinckrodt, Paris, Ky.) were ground with an analytical mill (model A-10, Tekmar, Cincinnati, Ohio). The ground particles were sieved with USA Standard Testing Sieves (ASTM-11 Specification, Fisher Scientific, Pittsburgh, Pa.) with openings of 53 µm (No. 270), 106 µm (No. 140), and 150 µm (No. 100) placed on a sieve shaker (model 18480, CSC Scientific, Fairfax, Va.). Chloroform and methylene chloride were furnished by Mallinckrodt. The mercury used in the porosimetry studies was triple-distilled (Bethlehem Apparatus, Hellertown, Pa.).

Processing Method.

Sieved salt particles were added to a polymer solution and the vortexed dispersion was cast in a 5 cm petri-dish. The salt, which was insoluble in the polymer solvent (and solution), was either sodium chloride, sodium tartrate or sodium citrate. The solvent for PLLA was chloroform or methylene chloride. Five different polymer/salt compositions were used: 1.25 g PLLA and 1.25 g salt (50 wt % salt); 1 g PLLA and 1.5 g salt (60 wt % salt); 0.75 g PLLA and 1.75 g salt (70 wt % salt); 0.5 g PLLA and 2 g salt (80 wt % salt); and 0.25 g PLLA and 2.25 g salt (90 wt % salt). The total amount of PLLA and salt was 2.5 g. For the first three compositions (50, 60, and 70 wt % salt), 8 mL solvent were used, whereas for the last two (80 and 90 wt % salt), 4 mL were used. For each composition, sieved salt particles of three different sizes, d, were employed: 0<d<53 µm; 53<d<106 µm; and 106<d<150 µm. The solvent was allowed to evaporate from the covered petri-dish over 48 hours. Residual amounts of solvent were removed by vacuum-drying at 100 µm Hg for 24 hours.

The resulting PLLA/salt composite membranes were heated at a temperature above the PLLA melting temperature to ensure complete melting of the polymer crystallites formed during the previous step.

The melted PLLA membranes with dispersed salt particles were either annealed (cooled down to room temperature slowly at a controlled rate) or quenched (cooled down rapidly) to produce semi-crystalline membranes with specific crystallinity and amorphous membranes, respectively.

The PLLA/salt composite membranes were immersed in 250 mL distilled-deionized water on a shaker at 100 rpm at 25° C. for 48 hours (the water was changed every 6 hours) to leach out the salt.

The salt-free PLLA membranes were air-dried for 24 hours, vacuum-dried at 100 µm Hg for 48 hours, and stored in a desiccator under vacuum until use.

The membranes produced without any heat treatment were semi-crystalline and had a reproducible degree of crystallinity. The heat treatment steps were optional and were only included to prepare membranes with desired crystallinity. Then, the petri-dish bottom was covered with an aluminum backed overlay (Cole-Parmer, Chicago, Ill.) to prevent sticking of the membrane to the glass bottom upon heating.

For the preparation of amorphous PLLA membranes, the PLLA/salt composite membranes, in covered glass petri-dishes, were heated in a convection oven (Model OV-490A-3, Blue M, Blue Island, Ill.) at 195° C. which is approximately 15° C. higher than the PLLA melting temperature, for 90 min. They were then taken from the oven and were rapidly immersed in liquid nitrogen for 15 min. The quenched membranes were thawed at 25° C. for 1 hour before proceeding.

The exact value of the initial salt weight fraction was calculated from weight measurements of the composite membranes before they were immersed in water to leach out the salt and after they had been vacuum-dried.

Mercury Intrusion Porosimetry.

The pore size distribution of PLLA membranes was determined by a mercury intrusion porosimeter (model Poresizer 9320, Micromeritics, Norcross, Ga.). A solid penetrometer with 5 mL bulb volume (Model 920-61707-00, Micromeritics) was used with porous membrane stripes of approximate dimension 1 cm×2 cm and weight in the range of 0.01–0.06 g. (For composite membranes, the sample weight was between 0.06 and 0.1 g.) The values of void volume and pore area were calculated from measurements of the mercury intrusion volume at different pressures. The filling pressure, $P_{min}$, of the penetrometer was 0.5 psi and the maximum pressure was 30 psi. At the pressure of 30 psi, the total intrusion volume had reached a plateau value.

Scanning Electron Microscopy (SEM).

Samples were coated with gold using a Sputter Coater (Model Desk II, Denton Vacuum, Cherry Hill, N.J.). The gas pressure was set at 50 mTorr and the current was 40 mA for a coating time of 75 s. A Hitachi (Model S-530) Scanning Electron Microscope was operated at a 15 kV voltage.

Differential Scanning Calorimetry (DSC).

A 7 Series Thermal Analysis system of Perkin-Elmer (Newton Centre, Mass.) was utilized to determine the thermal properties of PLLA/salt composite and PLLA porous membranes by measuring their melting and crystallization temperatures, and corresponding enthalpy changes. The sample weight for porous membranes was in the range of 2–12 mg, whereas for composite membranes approximately 20 mg of sample were tested. A heating or cooling rate of 10° C./min was applied in all studies. The degree of crystallinity, $X_c$, of a sample which exhibited no cold crystallization was calculated as $$X_c = H_m / \triangle H°_m$$

where $H_m$ designates the measured enthalpy of melting and $\triangle H°_m$ the enthalpy of melting for 100% crystalline polymer. For PLLA, $\triangle H°_m$=203.4 J/g. The peak temperature of a melting endotherm is the melting temperature, $T_m$.

A typical DSC test involved the heating of a sample from 20° C. to 200° C. to measure its melting temperature and enthalpy of melting. For the PLLA foams prepared without any heat treatment, the same sample was kept at 200° C., for 20 min, cooled to 20° C. kept at 20° C. for 10 min, and heated again to 200° C. (second heating). An exotherm was recorded at 100.2 (±1.7)° C. when the sample was cooled and at 103.9 (±2.5)° C. when heated for the second time, and the formed crystallites melted at 177.1 (±1.0)° C. All values are averages ± s.d. of fifteen samples.

Thermogravimetric Analysis (TGA).

The relative amounts of PLLA and salt of composite membranes were measured by Thermogravimetric Analysis (7 Series, Perkin-Elmer). In a typical experiment, 40 mg of material were heated from 150° C. to 550° C. at a constant rate of 10° C./min, and the normalized sample weight (expressed as fraction of the initial weight at 150° C.) was recorded as a function of temperature. For raw PLLA, the onset degradation temperature was 274.4 (±4.8°)° C. (average ± s.d. of three samples) and the peak degradation temperature was 315.2 (±3.0)° C. At 550° C., the normalized PLLA weight had reached a low plateau value of 0.0027 (±0.0012) or approximately zero. The salt weight fraction, $w_s$, of a PLLA/NaCl composite membrane was equal to the normalized weight at 550° C.

Neutron Activation Analysis (NAA).

Neutron Activation Analysis, which is one of the most sensitive analytical techniques for identification and measurement of trace elements, was used to determine residual amounts of sodium in PLLA porous membranes. For this technique, a sample material is irradiated with subatomic particles resulting in the conversion of some of its nuclei to radioactive isotopes. (For example, $^{23}$Na yields $^{24}$Na.) The produced isotopes decay at a characteristic rate emitting gamma-rays of characteristic energies. Membrane samples of approximately 40 mg were bombarded with thermal neutrons in a nuclear reactor (MITR-II) at the M.I.T. Nuclear Reactor Laboratory. Standard reference materials were analyzed along with the samples to calibrate the reactor and assess measurement accuracy. The sodium mass in a membrane sample was proportional to the activity of gamma-rays of energy 1368.5 keV. The minimum detection limit for the sodium weight fraction was $10^{-5}$.

Gel Permeation Chromatography (GPC).

The polymer molecular weight distribution was determined by Gel Permeation Chromatography (Perkin-Elmer, Series 10) equipped with a refractive index detector (Perkin-Elmer, LC-25). The samples were dissolved in chloroform and eluted through a Phenogel™ guard column (model 22824G, 50×7.8 mm, particles 5 µm, mixed bed, Phenomenex, Torrance, Calif.) and a Phenogel™ column (model GP/4446, 300×7.8 mm, particles 5 µm, mixed bed, Phenomenex)™ at a 1 mL/min flow rate. Polystyrene standards (Polysciences) were used to get a primary calibration curve. The values of the Mark-Houwink constants for PLLA, which were utilized to obtain the calibration curve and calculate the absolute polymer molecular weights, were K =5.45×10$^{-3}$ mL/g and α=0.73.

Results and Discussion

Figure 2A:
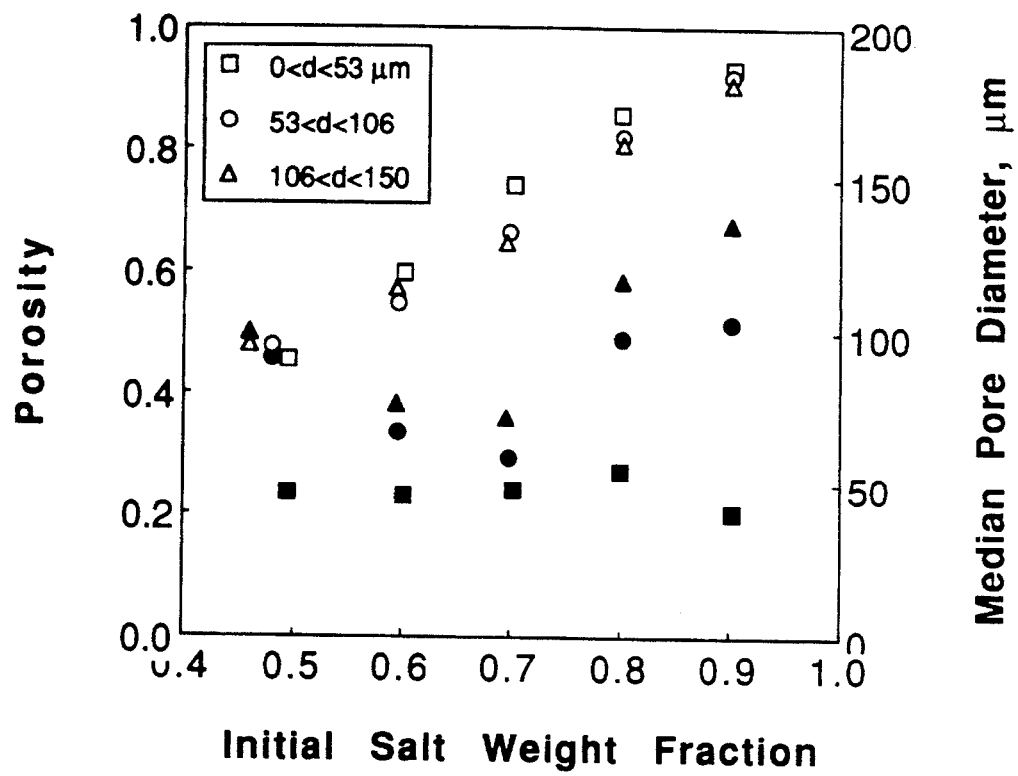
FIGS. 2A and 2B are graphs of the effect of initial salt weight fraction and salt particle diameter on the porosity, median pore diameter (microns), and surface/volume ratio (1/micron) of poly(lactic acid) (PLLA) membranes, prepared by the method described herein.
Figure 2B:
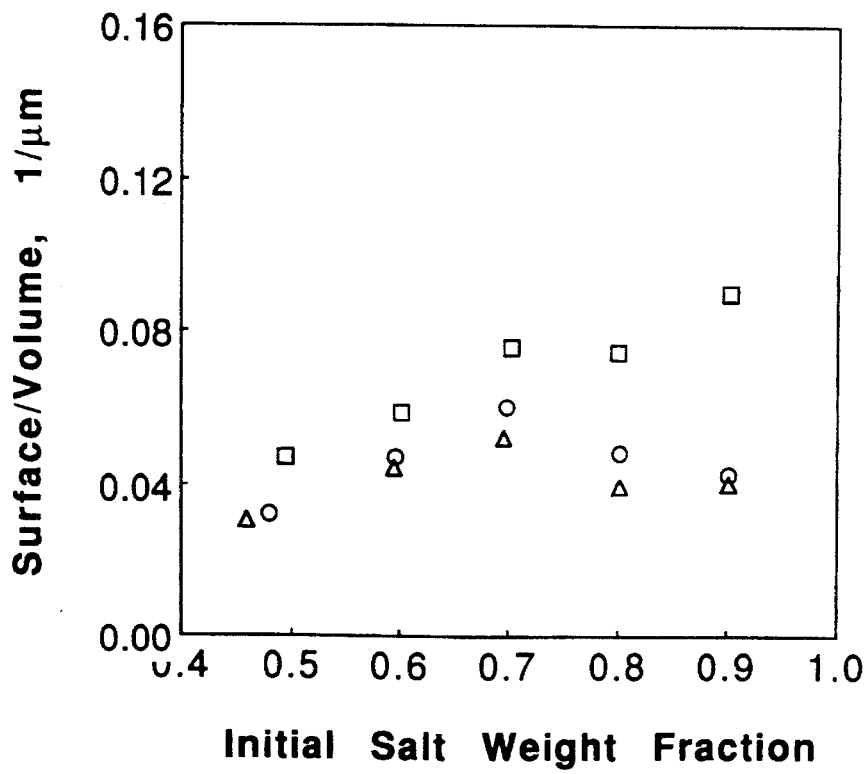
Figure 2C:
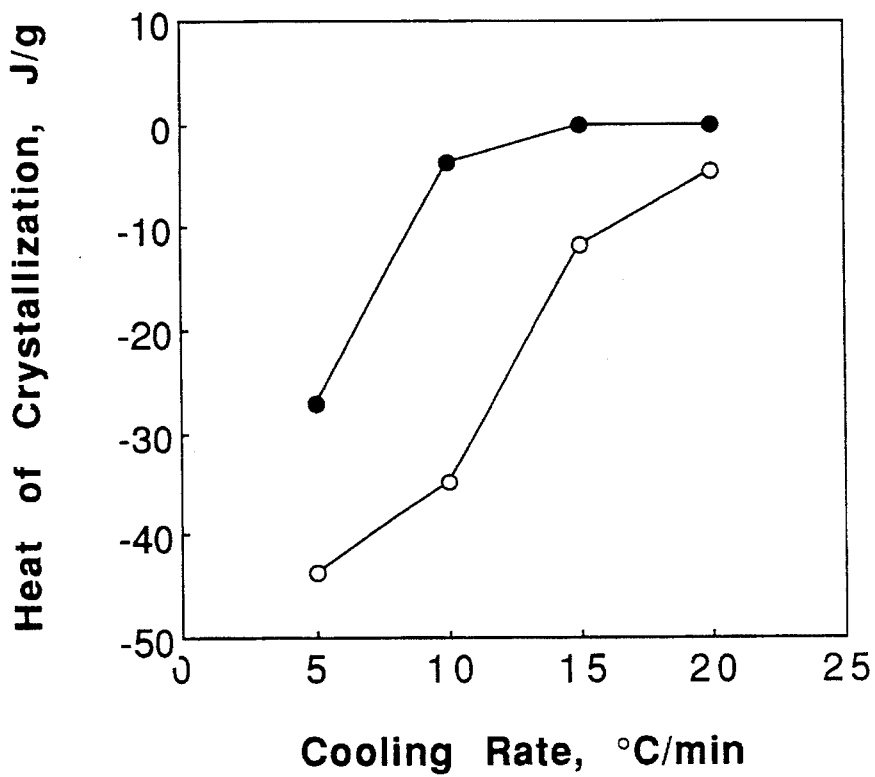
FIG. 2C is a graph showing the relationship between crystallinity of the membranes and the polymer cooling rate. The black circles represent membrane prepared with sodium chloride having a particle size diameter between 0 and 53 microns. The open circles represent non-porous control membranes prepared in the absence of salt.

Poly(L-lactic acid) (PLLA) porous membranes were prepared with sodium chloride, sodium tartrate, and sodium citrate particles, without any heat treatment to determine the effect of the initial salt weight fraction and particle size on the porosity, median pore diameter, and surface/volume ratio. The membrane porosity increased monotonically with the initial salt weight fraction, and was independent of the salt particle size, as shown by FIG. 2. By varying the initial sodium chloride weight fraction from 0.5 to 0.9, as shown by FIG. 2A, the porosity of the PLLA membranes increased from 0.45 to 0.93 microns when salt particles between 0 and 53 microns were used, from 0.48 to 0.92 microns when salt particles between 53 and 106 microns were used, and from 0.48 to 0.91 microns when salt particles between 106 and 150 microns were used. A similar dependence was also observed for PLLA membranes prepared with sodium tartrate or sodium citrate particles. FIG. 2C is a graph showing the relationship between crystallinity of the membranes and the polymer cooling rate.

The membrane porosity was calculated from measurements of the mercury intrusion volume. The cumulative void volume distribution (see FIG. 3) for foams prepared with sodium chloride particles between 106 and 150 microns in size exhibited only one inflection point, yielding a unimodal differential distribution which was described by the median value.

The salt particle size affected the pore size distribution. The median pore diameter of the porous membranes increased as the salt particle size increased. Nevertheless, it did not change with the initial salt weight fraction. For PLLA foams prepared with sodium tartrate particles between 0 and 53 microns, 53 and 106 microns, and 106 and 150 microns, the median pore diameter was 29.2 (±8.7), 66.3 (±7.3), and 115.6 (±18.4) microns, respectively (averages ± s.d. for foams prepared with 50, 60, 70, 80, and 90 wt % sodium tartrate).

The surface/volume ratio was a function of both initial salt weight fraction and particle size. It increased with the salt weight fraction (thus, it increased with membrane porosity), and was much larger for smaller salt particles (or pore diameters). For cylindrical pores, the surface/volume ratio scales to the inverse of pore diameter. The PLLA foams prepared with 90 wt % sodium citrate had a surface/volume ratio of 0.119 µm$^{-1}$ when particles between 0 and 53 microns were used, 0.081 µm$^{-1}$ when particles between 53 and 106 microns were used, and 0.064 µm$^{-1}$ when particles between 106 and 150 microns were used.

The salt type had no effect on the porosity, median pore diameter, and surface/volume ratio of the porous membranes. The foam properties were independent of the particular salt, and were only a function of the relative salt amount and salt particle size.

Membranes prepared with salt weight fractions of 70 wt % and higher had a uniform pore morphology and the pores were evenly distributed as evidenced by SEM photomicrographs of cross sections. The pores were interconnected, yielding an open-cell polymer foam. It is apparent that the larger the initial salt weight fraction the larger the foam porosity. By utilizing sieved salt particles of different sizes, membranes of the same porosity but with different pore diameters could be prepared. For example, PLLA foams prepared with 90 weight percent NaCl, of either particle size between 106 and 150 microns or 0 and 53 microns, pore size was either 0.91 or 0.93, respectively. However, when 50 or 60 wt % salt was used, asymmetric membranes were formed with a dense impermeable skin at the surface exposed to air. Here, the amount of polymer was much larger than that required to fill the crevices between the salt particles, which precipitated at the bottom of the petri-dish upon casting of the particle suspension.

The polymer/salt composite membranes were also porous. SEM photomicrographs of PLLA/NaCl membranes prepared with 80 wt % NaCl particles of different sizes reveal the existence of pores between salt particles. Polymer fibrils and/or flakes bridge the surfaces of adjacent salt particles. The porosity of PLLA/NaCl composite membranes increased with the salt weight fraction, and was larger for smaller particles. Therefore, pores were not only created by the dissolution of salt particles but also during solvent evaporation and polymer solidification.

Comparison of the salt weight fraction of PLLA/NaCl composite membranes measured by Thermogravimetric Analysis with that calculated from the weights of the composite membranes and the produced porous membranes was used to evaluate the polymer connectivity of composite membranes. The two values were identical for salt weight fractions in the range of 50 to 90 wt % and particle sizes between 0 and 53 microns, 53 and 106 microns, and 106 and 150 microns, confirming that no polymer was detached from the composite membrane during the salt-leaching step.

For salt weight fractions of 50, 60, and 70 wt %, 8 mL of chloroform were utilized whereas for 80 and 90 wt % salt 4 mL was used. The rationale for using 8 mL was to make the polymer solution less viscous and facilitate the casting procedure. Nevertheless, when 4 mL of chloroform were used for the weight fractions of 50, 60, and 70 wt %, the produced composite and porous membranes had approximately the same porosities as those prepared with 8 mL of chloroform. In the studies described above, the solvent for PLLA was chloroform. When methylene chloride, which is much more volatile than chloroform, was used, the composite and porous membranes had porosities similar to those prepared with chloroform. Chloroform was used as a standard solvent because of its slow evaporation, to improve the chances of forming homogeneous membranes.

All membranes prepared without any heat treatment exhibited no cold crystallization. The melting temperature(s), enthalpy of melting, and degree of crystallinity of four representative PLLA/NaCl composite and PLLA porous membranes are presented in Table I. The crystallites formed with solvent evaporation melted in the vicinity of 179.5 (±1.5)° C. (average melting temperature ± s.d. of fifteen samples). The crystallinity of the PLLA foams was the same as that of PLLA/NaCl composite membranes, and, therefore, was not altered during the dissolution of the NaCl particles by water. The PLLA crystallinity was also not affected by the different means of varying the porosity or the surface/volume ratio, as evidenced by the exact same linear relationship between the heat of melting and the salt weight fraction for all composite samples. The same results were also obtained when sodium tartrate or sodium citrate particles were used to prepare PLLA porous membranes.

TABLE I

Thermal properties of semicrystalline PLLA foams and PLLA/NaCl composite membranes.

| Type* | NaCl wt % | NaCl Range (μm,μm) | $T_m$ °C. | $DH_m$ J/g§ | $X_c$ |
|---|---|---|---|---|---|
| F | 70 | (106,150) | 181.7 | 45.8 | 0.225 |
| C | 70 | (106,150) | 179.1 | 54.6 | 0.268 |
| F | 80 | (106,150) | 181.0 | 47.5 | 0.233 |
| C | 80 | (106,150) | 179.8 | 47.3 | 0.233 |
| F | 90 | (106,150) | 178.6 | 47.8 | 0.235 |
| C | 90 | (106,150) | 179.3 | 52.4 | 0.257 |
| F | 90 | (0,53) | 177.2 | 49.9 | 0.245 |
| C | 90 | (0,53) | 176.0 | 44.4 | 0.218 |

*F = foam; C = composite.
§Calculated per gram of polymer.

By heat treating PLLA/NaCl composite membranes modifies their crystallinity. Using DSC, a sample was heated to 200° C. and cooled down to 20° C. at a constant rate. The heat of crystallization (or the amount of crystallites created) increased as the cooling rate decreased. The extent of crystallization was smaller for composite membranes than for salt-free PLLA. Nevertheless, by quenching the composite membranes with cooling rates of 20° C./min and higher, the polymer became amorphous.

Amorphous PLLA foams were prepared by cooling the PLLA/NaCl composite membranes very quickly from 195° to −195.8° C. (temperature of liquid nitrogen). Their DSC thermograms included a cold crystallization, and their degree of crystallinity was very close to zero. The glass transition temperature, $T_g$, did not vary with the processing conditions, and an average of 63.3 (±3.5)° C. was obtained. The melting temperature, $T_m$, was 175.4 (±1.6)° C. or 4.1° C. lower than that of the semi-crystalline foams.

The porosity of the amorphous PLLA membranes increased with the salt weight fraction and was independent of the salt particle size. The processing-structure relationship established for the semi-crystalline foams was also obeyed by the amorphous foams. Furthermore, the pore morphology of amorphous foams was similar to that of semi-crystalline. For large salt weight fractions, homogeneous foams with interconnected pores of desired diameter were prepared as demonstrated by SEM.

The efficacy of the salt-leaching step was evaluated by Neutron Activation Analysis. The residual sodium weight fraction of semi-crystalline and amorphous membranes prepared with sodium chloride decreased as the initial salt weight fraction increased and also as the salt particle size decreased. For initial sodium chloride weight fractions 60 wt % and higher, the residual sodium weight fraction was smaller than $10^{-3}$ for amorphous membranes and $10^{-4}$ for semi-crystalline ones. Consequently, all PLLA foams prepared by the particulate-leaching technique were essentially salt-free. The relatively high sodium content of membranes prepared with 50 wt % salt is probably due to the entrapment of salt particles within the dense polymer skin at the membrane surface.

From molecular weight measurements of raw PLLA and semi-crystalline foams by Gel Permeation Chromatography, it was concluded that water did not degrade the polymer while the salt was leached out. However, the molecular weight of amorphous PLLA foams was smaller than that of raw polymer. The decrease in the PLLA molecular weight, which also explains the melting temperature decrease, was caused by thermal degradation during heat treatment.

Method of Preparation of Three Dimensional Membrane Laminates and Seeding with Cells Because of the multiple functions they must fill, the physical and chemical requirements of templates for tissue ingrowth are numerous. In addition to being biocompatible, they must be adhesive substrates for cells, promote cell growth, and allow retention of differentiated cell function. In order to accommodate a sufficient number of cells for functional replacement, a cell transplantation device must have a large surface area for cell attachment. A uniformly distributed and interconnected pore structure is important so that cells are easily distributed throughout the device, and so that an organized network of tissue constituents can be formed.

High porosity, greater than 80% volume, provides adequate space for cell seeding, growth, and extracellular matrix (ECM) production.

The matrix scaffold is used to mimic its natural counterparts, the extracellular matrices (ECM) of the body. It serves as both a physical support and an adhesive substrate for isolated parenchymal cells during in vitro culture and subsequent implantation. As the transplanted cell population grows and the cells function normally, they begin to secrete their own ECM support. Concurrently, when using a biodegradable matrix material, the scaffold continuously degrades and is eliminated as the need for an artificial support diminishes. In the reconstruction of structural tissues like cartilage and bone, tissue shape is integral to function. Therefore, these scaffolds must be processable into devices of varying thickness and shape.

Preparation of Anatomical Shapes

Figure 3:
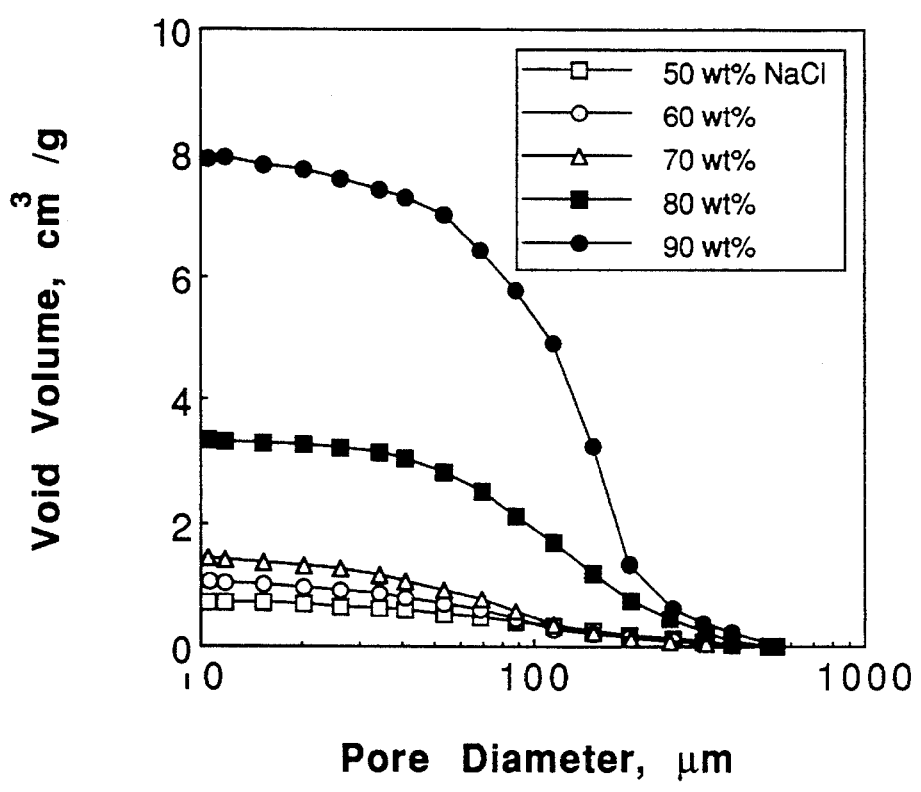
FIG. 3 is a graph of the cumulative void volume of semi-crystalline PLLA foams prepared with NaCl particles between 106 and 150 microns in size as a function of the pore diameter (microns) and the initial salt weight fraction: 50 wt % NaCl, open square; 60 wt %, open circle; 70 wt %, open triangle; 80 wt %, closed square; and 90 wt %, closed circle.

The membranes are processed into anatomical shapes, or foams, for use in reconstructive surgery or organ transplantation, as depicted in FIG. 3 (described in more detail below). A contour map 10 of the desired three dimensional shape is drawn and horizontally segmented into layers 20, corresponding to the depth of porous, biodegradable polymer membranes. The preferred thickness of the membrane is between 500 and 2000 microns. Computer programs, such as MATLAB™, available from The MathWorks, Inc., or Mathematica™, available from Wolfram Research, are preferably used to create the desired contour map.

Porous, biocompatible, polymer membranes 30 are prepared, for example, as described above, and are cut with scissors, a scalpel, a laser beam or other cutting means known to those skilled in the art or are molded to the predetermined two-dimensional shapes of the layers of the contour map as described above. The shapes are laminated in the proper orientation to form a three-dimensional structure 40 having the desired anatomical shape, shown schematically in FIG. 4 for the preparation of a nose-shaped foam.

Lamination of Membranes

Figure 4:
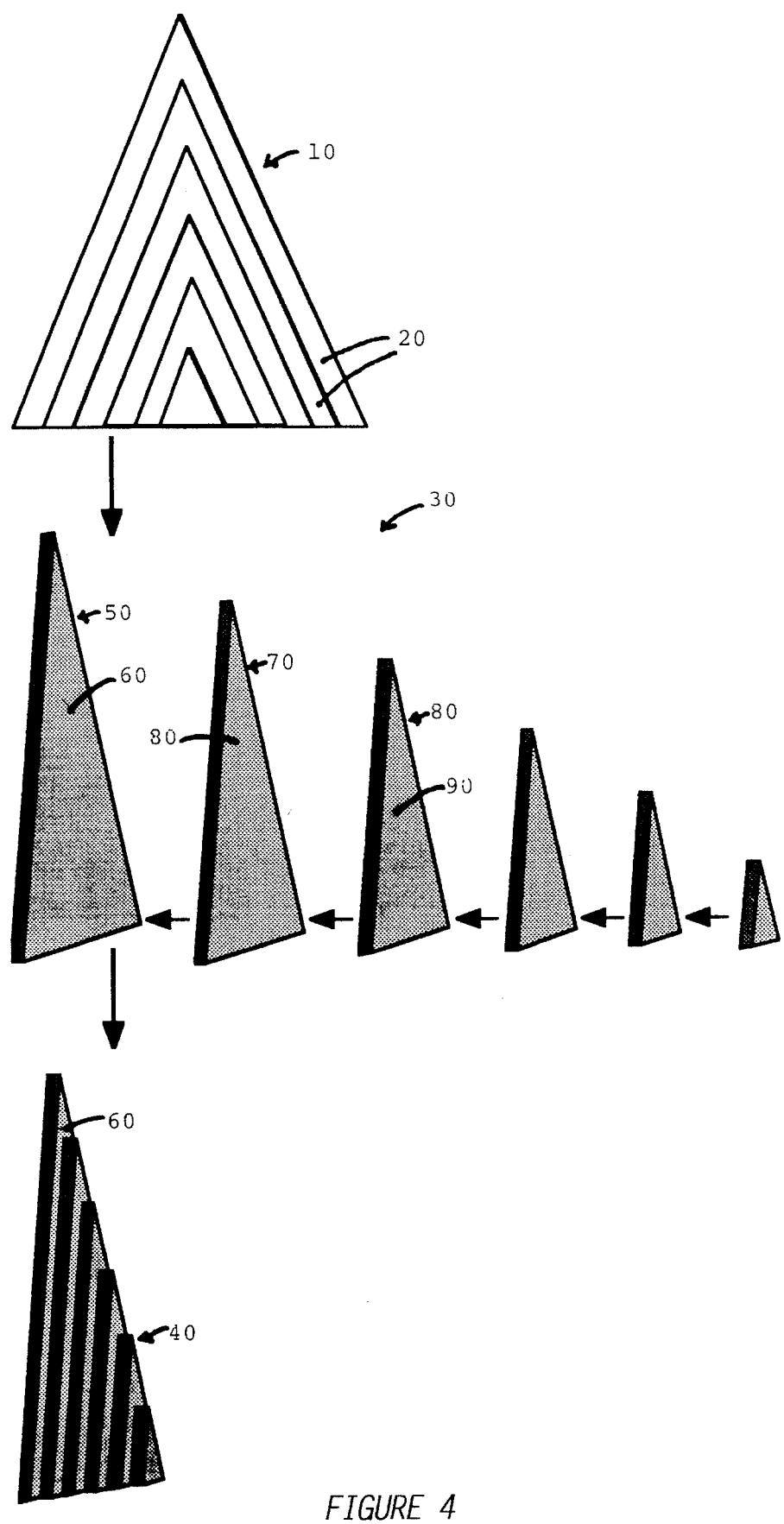
FIG. 4 is a schematic representation of the method of preparing of a biodegradable polymer having a human nose-like shape as described herein.

An absorbent material such as paper, cloth, or sponge is wetted with an organic solvent that will not adversely affect the polymer. Preferably, the organic solvent is chloroform or methylene chloride. Most preferably, the organic solvent is chloroform. Two or more membranes to be laminated are placed on the wetted absorbent material. Light pressure is applied to the exposed surface of each membrane for a sufficient amount of time to wet each bottom surface. For example, light pressure can be applied manually with forceps. Referring to FIG. 4, a first membrane 50 is removed from the absorbent material and is inverted on a dry surface so that the wetted surface 60 is exposed. A second membrane 70 is removed from the absorbent material and is placed on top of the first membrane so that the wet surface 80 is in contact with the wet surface 60 of the first membrane 50. The resulting bilayer laminate structure is gently compressed to ensure sufficient adhesion between the wet surfaces of the first and second membranes.

The procedure described above is repeated with the bilayer, or resulting multilayer laminate structure, and a subsequent membrane or other multilayer laminate structures until the desired three dimensional shape 40 is constructed.

The final laminated structure having the desired three-dimensional shape is dried, preferably by placing the structure in a lyophilizer for a sufficient amount of time to ensure complete solvent evaporation. Preferably, the laminate structure is lyophilized for approximately 24 hours.

Any crevices, apertures or refinements desired in the three-dimensional structure can be created by removing portions of the matrix with scissors, a scalpel, a laser beam or any other cutting instrument.

Characteristics of the Matrix

The resulting membranes are characterized by scanning electron microscopy (SEM), mercury porosimetry, and thermomechanical analysis, Specific examples are provided below.

Use of the Matrix for Reconstructive Surgery

The three-dimensional structure is specifically designed to provide a matrix for dissociated cells such as chondrocytes or hepatocytes to create a three-dimensional tissue or organ. Any type of cell can be added to the matrix for culturing and possible implantation, including cells of the muscular and skeletal systems, such as chondrocytes, fibroblasts, muscle cells and osteocytes, parenchymal cells such as hepatocytes, pancreatic cells (including Islet cells), cells of intestinal origin, and other cells such as nerve cells and skin cells, either as obtained from donors, from established cell culture lines, or even before or after genetic engineering. Pieces of tissue can also be used, which may provide a number of different cells types in the same structure.

The cells are obtained from a suitable donor or the patient into which they are to be implanted, dissociated using standard techniques, and seeded onto and into the matrix. These are optionally cultured in vitro prior to implantation. Alternatively, the matrix is implanted, allowed to vascularize, then the cells injected into the matrix. Methods and reagents for culturing cells in vitro and implantation of a matrix are known to those skilled in the art.

EXAMPLE 2

Preparation of Multi-layered Laminates of Porous Membranes.

Three-dimensional biodegradable polymer foams with precise anatomical shapes were constructed. The technique involves the lamination of highly-porous membranes of porosities up to 90%. Implants with specific shapes were prepared made of poly(L-lactic acid) and copolymers of poly(DL-lactic-co-glycolic acid) to evaluate feasibility. The produced biomaterials have pore morphologies similar to those of the constituent membranes. The pores of adjacent layers of laminated devices are interconnected, resulting in continuous pore structures. The compressive creep behavior of multi-layered devices is also similar to that of the individual layers.

Chondrocytes cultured in vitro onto fibrous poly(glycolic acid) for six weeks yield cell densities of the same order of magnitude as that reported from normal articular cartilage and produce cartilage matrix (i.e., sulfated glycosaminoglycan, collagen) at a high steady rate. Chondrocytes attached onto porous poly(L-lactic acid) for the same time period grew up to half the cellularity of normal cartilage. Chondrocytes grown onto these biodegradable polymers in vivo for a period of up to six months maintained the shape of the original scaffold and resulted in cartilage formation.

In order to utilize biodegradable and biocompatible polymers in reconstructive or plastic surgery as templates for chondrocyte attachment and transplantation, it is essential to process them into foams resembling the desired implants. Furthermore, for the generation of metabolic organs like liver and pancreas, large transplantation devices are needed to accommodate a sufficient cell mass for functional replacement.

Processing Technique

The methodology to process biodegradable polymer foams with anatomical shapes includes the following three steps:

(i) drawing the contour plot of the particular three-dimensional shape;

(ii) preparing highly-porous biodegradable membranes with the shapes of the contours; and (iii) laminating the constituent membranes with the proper order to form a structure with the desirable shape.

For example, the sequence of events involved in the preparation of an implant with a nose-like shape is illustrated in FIG. 4.

Materials

The polymers used were as described in Example 1. The polymer molecular weights were determined by gel permeation chromatography (Perkin-Elmer, Series 10, Newton Centre, Mass.) as $M_n=104,800$ ($M_w/M_n=1.13$) for PLLA, as $M_n=121,100$ ($M_w/M_n=1.16$) for PLGA 85/15, and as $M_n=82,800$ ($M_w/M_n=1.14$) for PLGA 50/50. $M_n$ stands for the number average molecular weight whereas $M_w$ for the weight average. Granular sodium chloride (Mallinckrodt, Paris, Ky.) was ground with an analytical mill (Model A-10, Tekmar, Cincinnati, Ohio). The ground particles were sieved with ASTM sieves placed on a sieve shaker (model 18480, CSC Scientific, Fairfax, Va.). Chloroform was furnished by Mallinckrodt. The mercury used in the porosimetry studies was triple-distilled (Bethlehem Apparatus, Hellertown, Pa.).

Methods

Contour Mapping

For simple geometries with equations $f(x,y,z)=0$ (with $z \geq 0$) describing the surface coordinates, the contours are defined by the family of equations $\{f(x,y,i\triangle z)=0, i=0,1,2, \ldots \}$. The parameter $\triangle z$ is equal to the thickness of the membranes to be laminated. For complex shapes, such as that of a human ear, the contours can be defined by sectioning a solid mold into slices of equal thickness.

Preparation of porous membranes

Biodegradable polymer membranes were prepared as described in Example 1. Briefly, 4.5 g of sieved sodium chloride particles (with sizes in the range of 250 to 500 μm) were added to a solution of 0.5 g polymer in 8 ml of chloroform, and the vortexed dispersion was cast in a 5 cm petri-dish. The solvent was allowed to evaporate from the covered petri-dish over 48 hours. Residual amounts of chloroform were removed by vacuum-drying at 100 μm Hg for 24 hours. For PLLA, the resulting composite membranes were immersed in 250 ml distilled-deionized water at 25° C. for 48 hours (the water was changed every 6 hours) to leach out the salt. For PLGA 85/15 and PLGA 50/50, the composite membranes were immersed in 250 ml distilled-deionized water at 37° C. for 96 hours (the water was changed every 12 hours) to leach out the salt. Afterwards, the salt-free membranes were air-dried for 24 hours, vacuum-dried at 100 μm Hg for 48 hours, and stored in a desiccator under vacuum until use.

Membranes of poly(L-lactic acid) were also prepared using half of the above quantities. The membranes cast with 0.25 g polymer, 2.25 g NaCl and 4 ml of chloroform were designated as PLLA/2.

The membranes prepared with poly(L-lactic acid) were semi-crystalline with a degree of crystallinity of 24.5% as measured by Differential Scanning Calorimetry (7 Series, Perkin-Elmer, Newton Centre, Mass.). The membranes of the copolymers PLGA 85:15 and 50:50 were amorphous.

Preparation of non-porous films

Polymer films were prepared and used to measure the contact angle between the different polymers and mercury. In a typical experiment, a solution of 0.5 g polymer in 4 ml of chloroform was cast in a 5 cm petri-dish. The chloroform evaporated from the covered petri-dish in a fume hood over 48 hours before vacuum-drying at 100 μm Hg for 24 hours. The produced films were stored in a desiccator under vacuum until use.

Lamination of porous membranes

Porous biodegradable membranes were cut to the contour shapes. A small quantity of 2–3 ml of chloroform was poured onto a few paper tissues (Kimwipes, Kimberly-Clark, Roswell, Ga.) so as to sufficiently wet them. Two membranes to be joined were placed on the wet tissues. Light pressure was applied on their top faces with the aid of forceps for 4–5 seconds, to ensure that they became adequately wet. Subsequently, one membrane was carefully removed and inverted on a dry surface, the wet face up. The other membrane was quickly picked up with forceps and was placed carefully on top of the first, the wet faces touching. Then, the resulting structure was squeezed gently, to ensure that the two portions were well glued together.

Every additional membrane layer was attached to the incomplete three-dimensional shape by following the procedure just described, until the desirable structure was obtained. The final laminated structure was placed in the lyophilizer for 24 hours to ensure complete solvent evaporation.

This method was used to prepare foams with anatomical shapes. For the characterization of laminated structures, circular disks of diameter 13.45 mm were cut with the aid of a cork borer and were laminated to make devices of two and three layers which were tested by the various experimental techniques described below.

Characterization

Methods were used as described in Example 1.

The porosity of the membranes and the laminated devices was also calculated from measurements of their surface density and their thickness. The thickness was measured with a micrometer (with accuracy ±10 μm). The surface density (in units of mass per area) was estimated from the weight of single or multi-layered disks of diameter of 13.45 mm.

Thermomechanical Analysis

A 7 Series Thermal Analysis System (Perkin-Elmer) was utilized in compressive creep studies of the laminated devices at 37° C. A constant force of 100 mN was applied to a sample using a quartz expansion probe with a circular base of 3.66 mm diameter (thus, yielding a compressive stress of 9.5 kPa) for 60 min. The force was then removed, and the sample was allowed to recover for 30 min. The sample strains at 60 and 90 min had reached a plateau value and were used to evaluate the creep behavior of laminated devices as compared to that of the constituent layers.

Porous Membranes for formation of laminates.

Highly-porous membranes were produced by the solvent-casting particulate-leaching technique. The physical properties of these membranes are presented in Table II. The membrane thickness depended on the polymer itself and also on its initial amount. The thickness of the PLLA/2 membranes was approximately half that of the PLLA ones prepared with twice as much polymer. The porosity of all membranes measured by mercury porosimetry was smaller than that calculated from surface density. The difference was minimum for PLLA (and PLLA/2) and maximum for PLGA 85:15 characterized with the largest (d=529 μm) and the smallest diameter d (d=377 μm), respectively.

In addition to the void volume, the pore area and median pore diameter were examined by mercury porosimetry for single membranes and for laminated devices of two and three membranes. A decrease was observed in the values of the void volume and pore area, and was explained by the dissolution of porous polymer in the vicinity of the glued surfaces followed by its solidification during solvent evaporation. By measuring the thickness of laminated devices, it was determined that there was a small decrease in the total thickness of 2- and 3-layer devices as compared to the sum of the values of the original layers. This total decrease was dependent on the particular polymer composition and scaled to the number of laminated layers. Nevertheless, the decrease of the void volume and pore area diminished as the number of laminated layers increased.

No appreciable weight decrease was recorded during each lamination (see Table II) and the surface density (defined as weight per unit area) was proportional to the number of laminated layers. Thus, one infers that the polymers close to the joined surfaces were dissolved in the presence of chloroform vapors and intermingled upon contact. Furthermore, this decrease of the void volume was not large enough to significantly affect the calculated values of the porosity. For example for PLGA 50:50, the decrease of the void volume from 4930 cm$^2$/g (1 layer) to 3360 cm$^2$/g (2 layers) resulted in a decrease of the porosity from 0.84 to 0.77. Also, no trend of increase or decrease in the median pore diameter can be identified. Finally, by inspecting the cumulative size distribution of PLLA laminated devices, one concludes that the pore morphology of multi-layered devices is similar to that of the constituent layers.

properties of the devices are indeed preserved during the lamination procedure.

SEM photomicrographs of a PLLA 3-layer laminated device and one of its layers before lamination show no discontinuity of the porous structure, nor could the junctions between adjacent devices be located. The same is also valid for a PLGA 85:15 3-layer laminated device, as shown by SEM photomicrograph. These photomicrographs further support the gentleness of the lamination process described above. In addition, from cell seeding studies into similar multi-layered devices, as described in more detail below, it was evident from the unhindered transport of fluids and cell suspensions across the interface of adjacent layers that the communication from layer to layer was not obstructed by the lamination process and that the interconnected pore structure was preserved.

The effect of the lamination process on the creep behavior of the polymer devices was evaluated by thermomechanical analysis. The strain measured for each device after 60 min of loading with 9.5 kPa of compressive stress. The strain measured for each of the PLLA, half-thickness PLLA (PLLA/2), and PLGA 85:15 devices was about 0.1, while the strain measured for the PLGA 50:50 devices was in the range between 0.4 and 0.5. The number of membranes which made up the device had no effect on the measured strain. After 60 min the stress was removed and the devices were allowed to recover unloaded for thirty minutes. For each material nearly 50% of the deformation was recovered. In addition, the rates of strain change during a compressive creep cycle were identical for devices with different numbers of layers. The lamination process does not cause a weakening of the polymer foam in response to compressive forces.

EXAMPLE 3

Preparation of multi-laminated porous membrane three dimensional structures.

Laminated devices with anatomical shapes were constructed for potential use in reconstructive or orthopedic surgery. An implant with a nose-like shape, which was prepared as schematically illustrated in FIG. 4, was created by lamination of six PLLA membranes of an average thickness of 1727 μm and total porosity of 88%. A photo-

TABLE II

| Polymer | Membrane | | | | Foam | | | | |
|---|---|---|---|---|---|---|---|---|---|
| Type (mg/cm$^2$) | Thickness* (μm) | Surface Density* | Porosity$^§$ | Porosity$^Y$ (mg/cm$^2$) | Thickness* (μm) | Surface Density* | Porosity$^§$ (mg/cm$^2$) | Porosity | Weight Decrease* |
| PLLA | 1727 ± 92 | 27.1 ± 1.1 | 0.88 | 0.83 | 3168 ± 223 | 51.1 ± 2.2 | 0.87 | 0.82 | 2.1 ± 0.4 |
| PLLA/2 | 904 ± 84 | 12.5 ± 0.5 | 0.89 | 0.84 | 1596 ± 85 | 23.9 ± 0.7 | 0.88 | 0.83 | 0.3 ± 0.1 |
| PLGA 85/15 | 1297 ± 119 | 24.0 ± 1.4 | 0.86 | 0.64 | 2427 ± 258 | 48.8 ± 1.8 | 0.84 | 0.58 | 0.0 ± 0.5 |
| PLGA 50/50 | 1867 ± 185 | 26.3 ± 2.0 | 0.90 | 0.84 | 3269 ± 274 | 52.6 ± 4.5 | 0.88 | 0.77 | −0.1 ± 0.1 |

*(average value ± standard deviation of five samples).
$^§$(as measured from the surface density).
$^Y$(as measured by mercury porosimetry).

Figure 5:
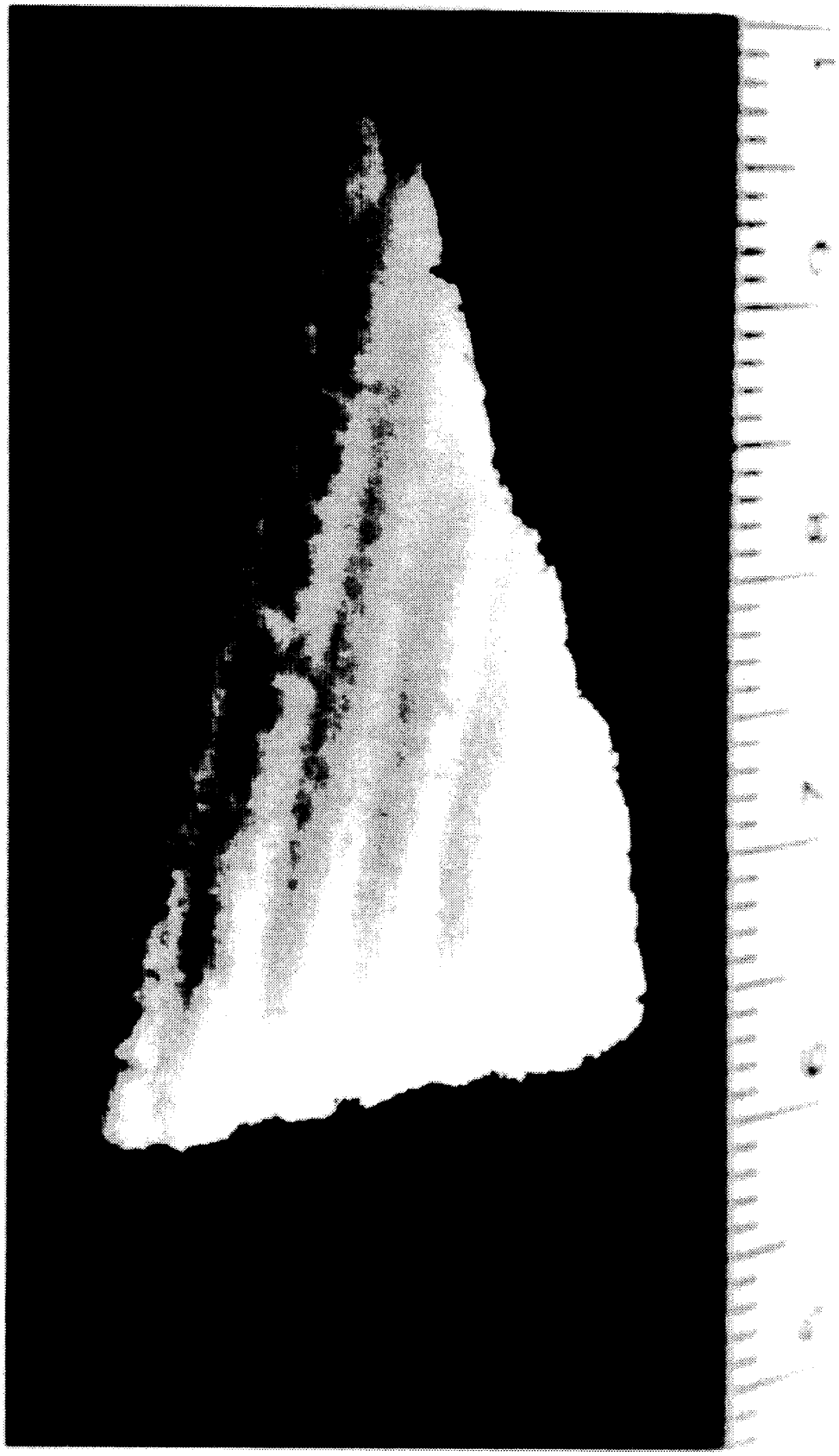
FIG. 5 is a photograph of a three-dimensional side view of a biodegradable polymer having a human nose-like shape, prepared by the method of FIG. 4.
Figure 6:
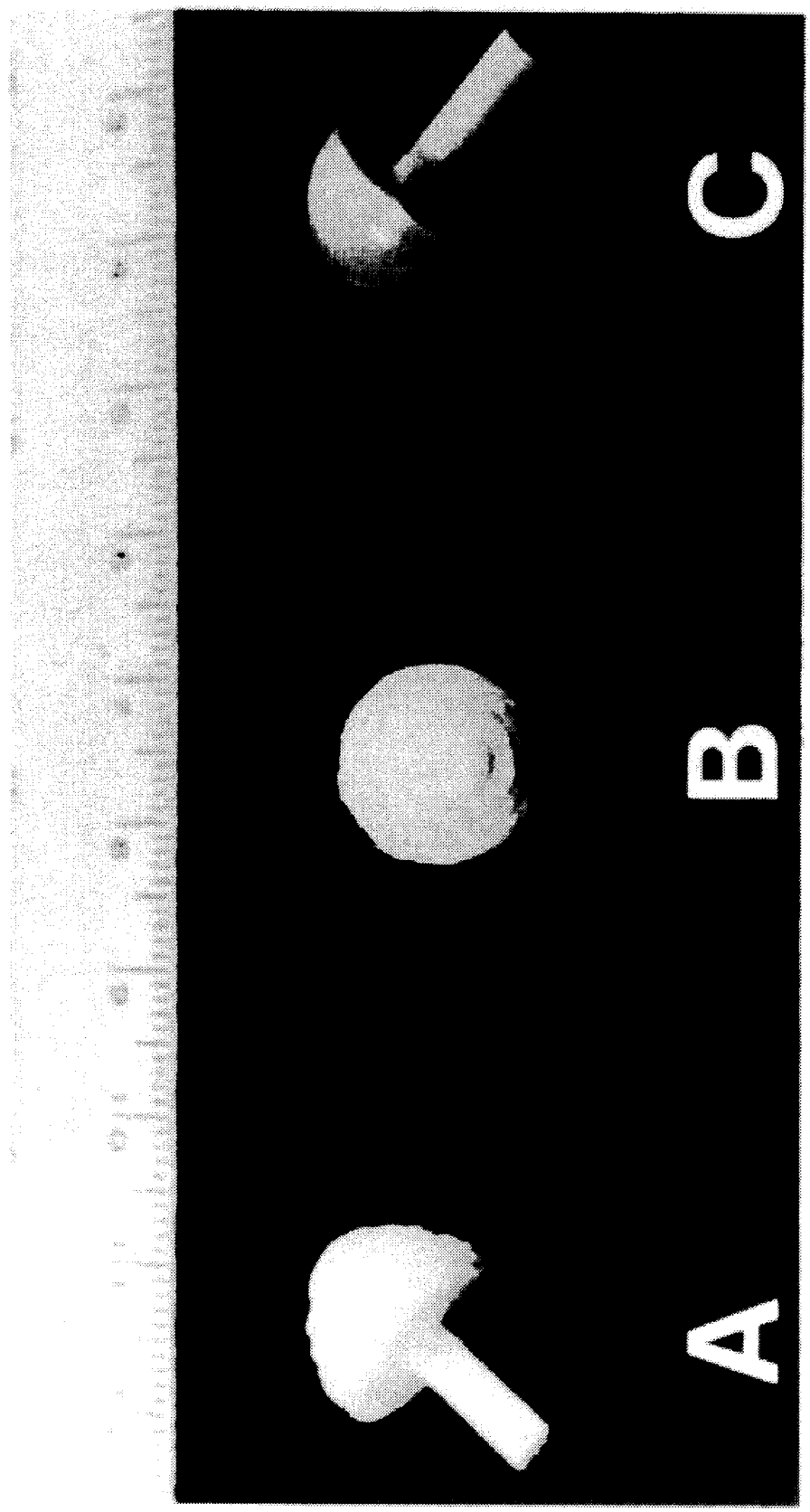
FIGS. 6A and 6B are photographs of a three-dimensional biodegradable polymer having the shape of metacarpal-phalangeal pieces for joint repair, prepared by the method provided herein.
FIG. 6C is a photograph of a side view of a prior art non-degradable medical implant having the shape of metacarpal-phalangeal pieces for joint repair.
Figure 7:
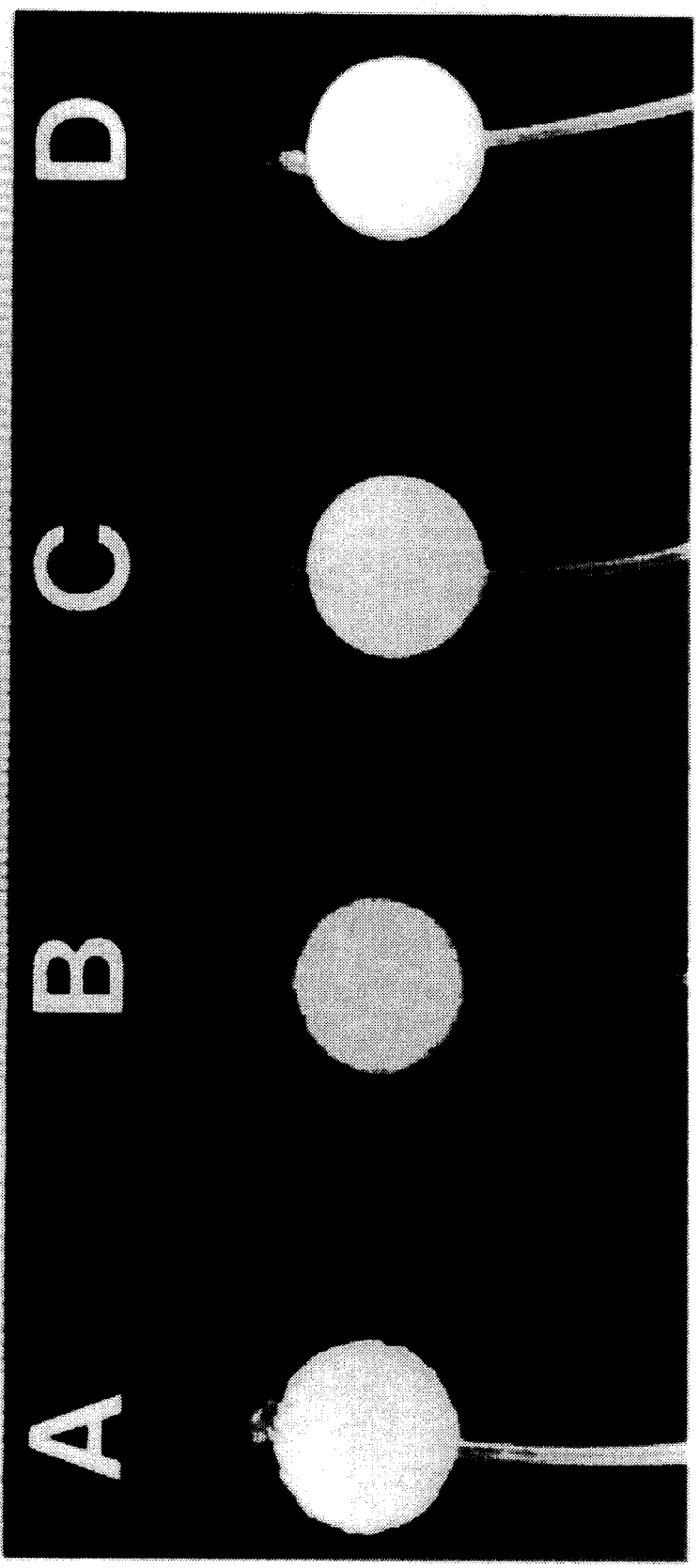
FIGS. 7A to 7D are photographs of hepatocyte transplantation devices made by lamination of three layers of PLLA (FIG. 7A), PLLA/2 (FIG. 7B), PLGA 85:15 (FIG. 7C), and PLGA 50:50 (FIG. 7D) with a catheter positioned in the middle of each device.

The above findings are crucial to the evaluation of the lamination technique for creating thick implantation devices. The lamination procedure is useful only if it preserves the uniform porous structure of the original foams. The boundary between two layers must be indistinguishable from the bulk of the device. These results show that bulk graph of the implant is shown in FIG. 5. Laminated foams from similar PLLA membranes were also processed with shapes of metacarpal-phalangeal pieces for joint repair, as shown in FIGS. 6A and 6B. The head of each foam was prepared by lamination of four layers (disks) with orientation perpendicular to the axis of symmetry of the hemisphere and the stem was created separately by lamination of two strips. The two pieces were joined together to form a foam with the desired pin-like shape.

The resulting laminated structure was mushroom-shaped in appearance. A photograph of a side view of the final structure is shown in FIG. 6A. A photograph of a top view of the final structure is shown in FIG. 6B. The resulting laminated structure compares favorably to a photograph of a side view of a prior art non-degradable medical implant having the shape of metacarpal-phalangeal pieces for joint repair shown in FIG. 6C.

Transplantation devices were also prepared for a variety of cells. Examples include devices for hepatocyte transplantation, as shown in FIGS. 7A–7D. Here, the lamination procedure was necessary to produce thick devices to accommodate a large number of hepatocytes for functional replacement. The devices were made of three layers with a catheter inserted in the center of each device as a route for injection of hepatocytes into the bulk of the polymer.

No delamination or failure of any devices due to developing shear stresses from surrounding tissues was detected from histological sections of a large number of harvested devices implanted in the mesentery of rats for a period of 35 days.

EXAMPLE 4

Distribution of cells within the three dimensional-structures.

The distribution of cells seeded into the devices of Example 3 via injection was modeled so as to maximize the device volume effectively employed in cell transplantation and determine the optimal surgical injection conditions. Wetting of the matrix prior to injection of the cells, use of a matrix with a pore size in excess of 150 microns, and injection of cells into the center of the device, were all important variables in insuring more even distribution of the cells within the matrix.

Construction of the Matrix.

Discs of 1.35 cm in diameter were cut out from polymer foams described above using a cork borer. The disks were glued to one another using small amounts of chloroform to wet adjacent surfaces. Devices consisted of three layers of PLLA foams and had an average thickness of 5000 (±72) µm (average ± s.d. of five measurements). Other materials of the poly(DL-lactic-co-glycolic acid) family (PLGA) were tested to ascertain the usefulness of membrane lamination on devices fashioned from these materials. Two copolymers of 85:15 and 50:50 molar ratios of lactic acid to glycolic acid were used (Medisorb, Cincinnati, Ohio). The surface coverage of each device was greater than or equal to 60% for each of the devices tested. All further evaluation was performed on devices of PLLA.

A 5 cm piece of medical grade silicone tubing (0.03 inches inner and 0.065 inches outer diameter; American Scientific Products, McGaw Park, Ill.) which served as the catheter was incorporated into the device across the diameter of the middle layer. A knot was tied at one end of the tubing. At a distance of 0.675 cm from the knot, two identical rectangular holes of length 1/16 inches were opened with a razor blade for bead injection. (The desired hole size was cut out with the aid of an english hexagonal key of size 0.035 inches which was put through the tubing.) The tubing was positioned in such a way that the two holes were at the center of the device and faced the edge. The completed device was lyophilized for 24 hours to remove residual chloroform. Devices to be used in cell experiments were sterilized using ethylene oxide gas for 12 hours.

Hepatocyte harvest.

Hepatocytes were harvested from Fisher rats (Charles River Breeding Laboratories, Wilmington, Mass.). Each rat was anaesthetized using methoxyflurane (Pitman-Moore, Washington Crossing, N.J.) and its abdomen was shaved, prepped with betadiene, and opened sterilely. The liver was isolated, heparinized with 100 U heparin (Elkins-Sinn, Cherry Hill, N.J.), and the portal vein was cannulated with a 23 gauge plastic intravenous cannula (Critikon, Tampa, Fla.). The inferior vena cava was transected, and the liver was flushed with 2 mL of sterile saline. Then, the liver was transferred to a sterile dish and was perfused with an oxygenated solution of 0.025% collagenase, Type II (Appel Products, West Chester, Pa.). The perfusion occurred for 20 min after which cells were dispersed in culture medium [William's E with 10 ng/mL EGF (Collaborative Research), 20 mU/mL insulin (Gibco, Grand Island, N.Y.), 5 nM dexamethasone (Sigma, St. Louis, Mo.), 20 mM pyruvate (Gibco), and 100 U/mL penicillin-streptomycin (Gibco)]. Debris was removed by centrifugation and washing in the culture medium. Cell viability at plating was 86% as determined by direct cell counts using trypan blue (Sigma).

Microbead injection experiments.

Dyed (red) monodisperse microparticles of polystyrene (Polysciences) ranging in size from 1 µm to 10 µm in diameter were injected into the transplantation devices. The devices were thoroughly wet prior to injection in ethanol for 10 min and then in 0.9 wt% saline solution for 10 min. The microparticle suspension was injected from a syringe through a 12 in catheter and 21 gauge needle (Minicath Infusion Set, Deseret, Sandy, Utah) and into the device's own catheter using a Harvard pump. The device was then sectioned and photographed with a zoom macroscope (Model M420, Wild Heerbrugg, Heerbrugg, Switzerland). Most of the devices were photographed while still wet. The surface area measurements of devices which were photographed after drying for 24 hours were compared only to other dry devices. The basic injection conditions used for testing were an injection rate of 0.5 mL/min, 6 µm in diameter beads, and catheter holds 1/16×1/16 in$^2$ at the center of devices with median pore diameter of 166 µm. Variables included the rate of injection of the microbead suspension, the bead diameter, the catheter hole position and size, the device pore size and the device thickness. Triplicates were run for each variable tested. Acid orange 8 dye (0.5%) (Sigma) was injected into some of the devices in a similar manner.

Hepatocyte injection and histology.

A suspension of $1.0 \times 10^7$ cells/mL was injected into each device in a procedure identical to that used for microbead injection. The cellular experiments were performed under sterile conditions. Samples were prepared for histology by removing the culture medium from the sample dish and fixing the device in 3% glutaraldehyde (Polysciences) for 15 min. The samples were rinsed and stored in 10% neutral buffered formalin solution (Sigma) until sectioning and staining. Samples were sliced into thin sections and stained with hematoxylin & eosin (H&E) which allowed for visualization of cells and cell nuclei.

Image analysis.

Image analysis was performed using a Magiscan 2 Image Analysis System (Joyce-Loebl, Tyne & Wear, England) equipped with a Polaroid MP-4 Land Camera. Polaroid photographs of the devices at 7.875 magnification were analyzed for the percentage of the top surface area of 1.43 cm$^2$ which was colored red by the presence of dyed microspheres. The photograph was analyzed by interfacing the Polaroid camera to the black and white video monitor of the image analysis system. The grey scale of the image was segmented on the video screen. Any part of the image that was dark (i.e., red from the dyed microspheres) was colored white. The detected area of each white region was determined by the number of non-zero pixels which constituted the feature region. The sum of the detected areas was recorded as the total area of dyed microsphere distribution for the top surface of the device.

Microbead distribution throughout the device volume was measured by the area of bead distribution on the external surface of the device. It was this surface which was furthest away from the injection site, therefore, it represented the distribution of microbeads at the most distant site from where the microbeads were injected. This surface area was also used because it is possible to photograph it without disrupting the device. Significant differences in surface area of coverage were found for devices which were photographed while still set versus those photographed while still dry. Significant variations in the microbead distribution were observed for many of the variables tested. These results are summarized below.

The Model microparticles proved to be a fast, simple way in which to determine the parameters that are important for seeding cells in porous devices. Because isolated cells are spherical in suspension, the microbeads are expected to provide a general idea of the behavior of a cell suspension to a first approximation. This system allows for the optimization of injection conditions without the complication and waste of using a large and steady supply of animal cells. The use of dyed microspheres permitted rapid determination of particle distribution within the device.

Polymeric microparticles were also used to examine the internal pore structure of the cell transplantation devices. It was evident on cross-sections that the lamination process did not cause obstruction of the flow of fluids or microspheres between pores of adjacent layers. In thick devices constructed of five polymer membrane layers, the outermost layers were not adjacent to the catheter and showed dye and microsphere distribution that were consistent with the distribution in the rest of the device.

Prewetting devices.

Injection of liquid or microsphere suspension into dry devices was not useful for the purpose of seeding. The dry device prohibited entry of the dye solution into its porous structure. The device which was pre-wetted with ethanol allowed the rapid transport of dye into the pores. All further revaluation was completed on devices which were pre-wetted according to this protocol.

Because of the high hydrophobicity of PLLA, the dry PLLA devices did not allow entry of liquid in the air-filled porous structure. The prewetting procedure using ethanol was adopted to overcome this problem. Ethanol readily entered the porous structure of the device, after which it was readily displaced by water.

Device uniformity.

Devices injected either with acid orange 8 dye or with microparticle suspension were studied using device cross sections and subjected to visual examination. It was observed that the pores of adjacent layers of the laminated devices were well interconnected as evidenced by the rapid and unhindered transport of both dye solution and model beads across the interface of adjacent layers. Thicker devices were constructed by adding an additional porous layer to the top and bottom surfaces of each device.

Catheter hole size and placement.

Two different configurations of catheter holes were tested. The first configuration had two holes placed one centimeter apart and on opposite sides of the catheter. The second configuration had both holes at the center of the device. Microparticles injected through the catheter of the first configuration left the catheter through the hole closest to the catheter entrance to the device. They did not reach the second hole under experimental injection conditions (0.5 mL/min). In addition, there was a great deal of particle leakage out of the edge of the device nearest to the first hole. In this case, particle distribution was limited to an approximately spherical volume near the first hole covering only 27.66 (±0.07) % of the surface (photographed dry). Devices of the second configuration showed a much larger distribution of particles radially outward from the center of the device, and leakage from the edges was drastically reduced. The surface area of coverage was 38.52 (±2.25) % of the total (dry). This second configuration was used in the remainder of the devices tested.

Devices with catheter holes $2/16$ inches in length showed a uniform bead distribution over 72.66 (±12.41) % of the surface. Devices with the standard hole size of $1/16$ inches also had a uniform bead distribution covering an average of 59.04 (±8.90) % of the surface area. Although one might infer that larger catheter holes result in bigger surface coverage, no such conclusion can be reached from these data as the difference between the measured values of surface coverage was of the same order of magnitude as the calculated standard deviation rate.

Injection rate.

Trials utilizing the fastest injection rate (1.0 mL/min) were superior in bead distribution demonstrating a mean detected surface area of 59.26 (±5.98) % of the whole, and even dispersion over most of the surface area. The slowest injection rate (0.25 mL/min) showed poorer average distribution of 45.76 (±8.61) % with the beads remaining in the center of the device.

Particle size and pore size.

Microspheres injected into devices with a median pore diameter of 166 μm were dispersed in a spherical volume about the center of the device where the catheter holes were located. The percent surface area of distribution was 59.04 (±8.90) %. Very little radial dispersion of the beads was observed in the devices with median pore diameter of 126 μm. An axial channeling along the length of the catheter was seen instead. The surface area of distribution of beads in these devices was 36.81 (±7.34) % covered. A high degree of microparticle leakage from the device at both the entrance and exit of the catheter was observed.

Monodisperse beads of 1 μm and 10 μm in diameter did not show any difference in the average surface area of distribution. However, the 10 μm beads were distributed at the device surface in a patchy manner.

Factors which were found to be very important in achieving uniform microbead distribution included the particle size to pore size ratio, the placement of catheter holes, and the suspension injection rate. The catheter hole placement had a marked influence on the bead distribution. When the holes were positioned near either end of the device, the beads did not reach the more distant half of the device. A great deal of bead leakage occurred using this configuration. Positioning both holes at the center gave a much wider bead distribution.

Ex Vivo Experiments.

Hepatocytes injected into transplantation devices under standard conditions were well distributed throughout the devices as indicated by the coloring of the external surfaces. Thin sections revealed numerous hepatocytes at cross-sections taken at distances of ¼ inches from the center of the devices both parallel and perpendicular to the catheter. Some of the hepatocytes appeared to be injured. All were spherical in shape, and none were flattened out along the implant material.

Because mammalian cells are fragile and easily disrupted by shear stresses one is inclined to use injection rates that are as low as possible. However, the results of the microbead studies showed that as injection rate was increased over a small range, the microbead distribution in the devices dramatically improved. Most likely, the higher flow rates involve more turbulence, and improved particle transport. The best injection rate for cell suspensions must necessarily be determined by the careful balancing of the two requirements. The presence of damaged hepatocytes in the histological sections from the ex vivo experiments, indicates that this variable is one which is tightly constrained.

The results of the experiments also suggest that the pore size-to-particle size ratio is an important determinant of microbead distribution because of the physical obstruction of flow which occurs. Notably, variation of the pore size and variation of the particle size within the range studied have different effects on the particle distribution. Pore size is important not only in cell seeding, but also in the induction of tissue growth in the culture period following seeding, and in vivo.

Modifications and variations of the methods and compositions of the present invention will be obvious to those skilled in the art from the foregoing detailed description. Such modifications and variations are intended to come within the scope of the appended claims.

We claim:

1. A method of producing a biocompatible porous membrane comprising the steps of:

a) dispersing particles of a material selected from the group consisting of salts of an organic or inorganic compound, proteins, and polysaccharides having a diameter of less than 500 microns in a biocompatible polymer solution to form a particle and polymer composition having an initial polymer dry weight fraction of between 0.1 and 0.5 weight percent, wherein the polymer is dissolved in a non-aqueous solvent and is selected from the group consisting of poly(alpha esters), polyanhydrides, polyorthoesters, poly(vinyl alcohol), and ethylene vinyl acetate;

b) leaching the polymer solvent from the composition to form a membrane;

c) dissolving the particles from the membrane with a solvent for the particles without dissolving the polymer; and d) removing the solvent for the particles by evaporation to form a porous membrane wherein the porosity is greater than 50%; and e) modifying the crystallinity of the polymer by heating of the polymer.

2. The method of claim 1 wherein the crystallinity of the membrane is modified by melting the polymer in the composition and then cooling the composition before the dissolving step.

3. The method of claim 1 wherein the polymer is a biodegradable polymer selected from the group consisting of poly(hydroxy acids), polyanhydrides, and polyorthoesters.

4. The method of claim 1 wherein the particles have a diameter between 100 and 500 microns.

5. The method of claim 1 wherein the particles are added to the polymer solution in the range from 4.2 to 21.1 weight percent.

6. The method of claim 1 wherein the particle material is a biocompatible sodium salt.

7. The method of claim 1 wherein the membrane is cast into a mold having a desired shape.

8. The method of claim 1 wherein the membrane is between 500 and 2000 microns in thickness.

9. The method of claim 4 wherein the membrane has a porosity of greater than 90% in the form of interconnected interstitial spaces or pores.

* * * * *